United States Patent [19]
Wahl et al.

[11] Patent Number: 5,449,688
[45] Date of Patent: Sep. 12, 1995

[54] METHOD OF TREATING CHRONIC INFLAMMATORY DISEASES

[75] Inventors: Sharon M. Wahl, Gaithersburg, Md.; Janice B. Allen, Angier, N.C.; Nancy L. McCartney-Francis, Gaithersburg, Md.

[73] Assignee: The United States of America as represented by the Department of Health and Human Services, Washington, D.C.

[21] Appl. No.: 39,849

[22] Filed: Mar. 30, 1993

[51] Int. Cl.$^6$ .................... A61K 31/04; A61K 31/195
[52] U.S. Cl. ................... 514/546; 514/564; 514/565; 514/634
[58] Field of Search ................ 514/546, 564, 565, 634

[56] References Cited

U.S. PATENT DOCUMENTS

| | | | |
|---|---|---|---|
| 5,028,627 | 7/1991 | Kilbourn et al. | 562/560 |
| 5,059,712 | 10/1991 | Griffith | 514/565 |

FOREIGN PATENT DOCUMENTS

| | | |
|---|---|---|
| 0446699 | 9/1991 | European Pat. Off. . |
| WO90/00900 | 2/1990 | WIPO . |
| WO91/00349 | 1/1991 | WIPO . |
| WO92/02253 | 2/1991 | WIPO . |
| WO91/04023 | 4/1991 | WIPO . |

OTHER PUBLICATIONS

Ialenti et al. *European Journal of Pharmacology*, 211 (1992) 177–182.
Wahl et al. In Molecular Pathogenesis of Periodontal Disease (1994) chapter 16 pp. 183–190.
Wahl *In Inflammation: Basic Principles and Clinical Correlates*, (1988) chapter 47 pp. 841–860.
Schmidt, *The Lancet*, (1992) vol. 339, p. 986.
Sano, *J. Clin. Invest.*, (1992) vol. 89, pp. 97–108.
Hines, *Immunomethods* (1993) vol. 3, pp. 13–22.
Allen, *Cytokine*, (1991) vol. 3(2), pp. 98–106.
Wahl, *Progress in Inflammation Research and Therapy* (1991) pp. 29–34.
Remmers, *Growth Factors*, (1990), vol. 2, pp. 179–188.
McCartney-Francis, *J. Exp. Med.*, (Aug. 1993) vol. 178, pp. 749–754.
Mulligan, Br. *J. Pharmacology*, (Dec. 1992) vol. 107 (4), pp. 1159–1162.
Umans, Eur. *J. Pharmacology* (1992) vol. 210, pp. 343–346.
Stefanovic-Racic, et al., "Nitric Oxide and Arthritis" in Arthritis and Rheumatism, vol. 36, No. 8 (Aug. 1993) pp. 1036–1044.
"Nitric Oxide in the Clinical Arena", *The Lancet*, 338, 1560–1561 (Dec. 1991).
Bernard et al., "Activated Macrophages Depress the Contractility of Rabbit Carotids via an L-Arginine/Nitric Oxide-dependent Effector Mechanism", *Clin. Invest.*, 89, 851–860 (Mar. 1992).
Bredt et al., "Cloned and Expressed Nitric Oxide Synthase Structurally Resembles Cytochrome P-450 Reductase", *Nature*, 351, 714–718 (Jun. 1991).
Duarte et al., "Peripheral Analgesia and Activation of the Nitric Oxide-cyclic GMP Pathway", *Journal of Pharmacology*, 186, 289–293 (1990).
Hibbs et al., "L-Arginine is Required For Expression of the Activated Macrophage Effector Mechanism Causing Selective Metabolic Inhibition in Target Cells", *The Journal of Immunology*, 138, 550–565 (Jan. 1987).
Hughes et al.; "Evidence that Endogeneous Nitric Oxide Modulates Oedema Formation Induced by Substance P", *European Journal of Pharmacology*, 191, 481–484 (1990).
Huot et al., "Role of Reactive Nitrogen Intermediate (List continued on next page.)

*Primary Examiner*—Marianne M. Cintins
*Assistant Examiner*—William R. A. Jarvis
*Attorney, Agent, or Firm*—National Institutes of Health

[57] ABSTRACT

The present invention provides a method for treating chronic inflammatory conditions, including autoimmune diseases by administering an effective amount of an agent, such as a nitric oxide synthase inhibitor, a nitric oxide scavenger, or an inhibitor of tetrahydrobiopterin synthesis, to decrease the amount of nitric oxide present at the site of inflammation.

11 Claims, 8 Drawing Sheets

OTHER PUBLICATIONS

Production in Alveolar Macrophage-Mediated Cytostatic Activity Induced by Bleomycin Lung Damage in Rats", *Cancer Research*, 50, 7863–7866 (Dec. 15, 1990).

Huot et al., "Formation of Nitric Oxide Hemoglobin in Erythrocytes Co-Cultured with Alveolar Macrophages Taken From Bleomycin Treated Rats", *Biochem. Biophys. Res. Commun.*, 182, 151–157 (Jan. 15, 1992).

Kaiser et al., "Depression of Endolthelium-Dependent Relaxation in Aorta From Rats With *Brugia pahangi* Lymphatic Filariasis", *Circulation Research*, 68, 1703–1712 (Jun. 1991).

Knowles et al., "Formation of Nitric Oxide from L-Arginine in the Central Nervous System: A Transduction Mechanism For Stimulation of the Soluble Guanylate Cyclase", *Proc. Natl. Acad. Sci. USA*, 86, 5159–5162 (Jul. 1989).

Kolb et al. "Suppression of Low Dose Streptozotocin Induced Diabetes in Mice by Administration of a Nitric Oxide Synthase Inhibitor", *Life Sciences*, 49, PL–213—PL–217 (1991).

Kröncke et al. "Activated Macrophages Kill Pancreatic Syngeneic Islet Cells Via Arginine-Dependent Nitric Oxide Generation", *Biochemical and Biophysical Research Communications*, 175(3), 752–758 (Mar. 1991).

Kubes et al., "Nitric Oxide: An Endogeneous Modulator of Leukocyte Adhesion", *Proc. Natl. Acad. Sci. U.S.A.*, 88, 4651–4655 (Jun. 1991).

Kubrina et al., "Formation of Nitric Oxide in Animal Tissues During Inflammatory Process", *Biull Eksp. Biol. Med.*, 107 (1) 31–33 (Jan. 1989).

Lancaster, "Nitric Oxide in Cells", *American Scientist*, 80, 248–259 (May–Jun. 1992).

Lyons et al. "Molecular Cloning and Functional Expression of an Inducible Nitric Oxide Synthase from a Murine Macrophage Cell Line", *The Journal of Biological Chemistry*, 267(9), 6370–6374 (Mar. 1992).

MacIntyre et al., "Osteoclastic Inhibition: An Action of Nitric Oxide not Mediated by Cyclic GMP", *Proc. Natl. Acad. Sci. U.S.A.*, 88, 2936–2940 (Apr. 1991).

McCall et al., "Induction of Nitric Oxide Synthase in Rat Peritoneal Neutrophils and its Inhibition by Dexamethasone", *European Journal of Immunology*, 21, 2523–2527 (1991).

Moncada et al., "Biosynthesis of Nitric Oxide From L-Arginine", *Biochemical Pharmacology*, 38(11), 1709–1715 (1989).

Murray et al., "L-Arginine-Dependent Reactive Nitrogen Intermediates and the Antimicrobial Effect of Activated Human Mononuclear Phagocytes", *Journal of Infectious Diseases*, 165, 513–517 (1992).

O'Connor et al., "Glucocorticoids Inhibit the Induction of Nitric Oxide Synthase and the Related Cell Damage in Adenocarcinoma Cells", *Biochim. Biophys. Acta.*, 1097, 227–231 (1991).

Palmer et al., "L-Arginine is the Physiological Precursor For the Formulation of Nitric Oxide in Endothelium-Dependent Relaxation," *Biochem. Biophys. Res. Commun.*, 153(3), 1251–1256 (Jun. 1988).

Radomski et al., "Glucocortoids Inhibit the Expression of an Inducible but not the Constitutive, Nitric Oxide Synthase in Vascular Endothelial Cells", *Proc. Natl. Acad. Sci. U.S.A.*, 87, 10043–10047 (Dec. 1990).

Shultz et al., "Synthesis and Action of Nitric Oxide in Rat Glomerular Mesangial Cells", *Am. J. Physiol.*, 261, F600–F606 (1991).

Snyder et al., "Biological Roles of Nitric Oxide", *Scientific American*, 68–77 (May 1992).

Stadler et al., "Articular Chondrocytes Synthesize Nitric Oxide in Response to Cytokines and Lipopolysaccharide", *Journal of Immunology*, 147(11), 3915–3920 (Dec. 1991).

Tare et al., "Hyperpolarization and Relaxation of Arterial Smooth Muscle Caused by Nitric Oxide Derived from the Endothelium", *Nature*, 346, 69–71, 1990.

Toda et al., "Endothelium-derived Relaxing Factor (EDRF)", *Nippon Yakurigaku Zasshi*, 95(6), 295–308, Jun. 1990.

Weissman et al., "$N^G$-Nitro-L-Arginine Enhances Neuronal Death Following Transient Forebrain Ischemia In Gerbils", *Neuroscience Letters*, 146, 139–142 (1992).

Xie et al., "Cloning and Characterization of Inducible Nitric Oxide Synthase from Mouse Macrophages", *Science*, 256, 225–228 (Apr. 1992).

Zielasek et al., "Production of Nitrite by Neonatal Rat Microglial Cells/Brain Macrophages", *Cellular Immunology*, 141, 111–120 (1992).

Corbett et al., *Diabetes*, vol. 41, Apr. 1992, pp. 552–556.

Mulligan et al., *Medline Abstract No.* 93104992, 1992.

Umans et al., Medline Abstract No. 92307003, 1992.

* DAHP = 2, 4 diamino-6-hydroxy-pyrimidine 5,449,688

1

METHOD OF TREATING CHRONIC INFLAMMATORY DISEASES

TECHNICAL FIELD OF THE INVENTION

The present invention relates to a method of treating acute and chronic inflammatory conditions, including autoimmune diseases. In particular, the present invention relates to a method of reducing the amount of nitric oxide present at a site of inflammation by administering a nitric oxide synthase inhibitor, a nitric oxide scavenger, or an inhibitor of tetrahydrobiopterin synthesis.

BACKGROUND OF THE INVENTION

Inflammatory and immune reactions depend upon the recruitment and migration of circulating leukocytes to sites of injury or antigen exposure. Accumulation and activation of leukocytes result in the generation of numerous cytokines, growth factors, enzymes, and mediators, which participate in the further recruitment and activation of leukocytes, thereby augmenting and perpetuating the defense of the injured or antigen-exposed mammal.

When a particular type of leukocyte, namely the macrophage, is activated by bacteria, bacterial products, T lymphocyte-derived cytokines, and antigens, it responds by converting arginine into nitric oxide (NO). NO is just one of a number of highly toxic free-radicals, which include oxygen ($O_2-$), peroxide ($H_2O_2$), and hydroxyl radicals (OH·). When released from macrophages as part of the host defense mechanism, NO contributes to leukocyte killing of bacteria, fungi and tumor cells. The extracellular release of NO from other cells and tissues, such as endothelium, may cause vasodilation and tissue damage.

NO is produced by the action of a NO synthase. Some cells, such as macrophages, express an inducible NO synthase, which produces large quantities of NO upon stimulation. In contrast, cells, such as neurons and endothelial cells, possess a constitutive form of this enzyme. In other words, the NO synthase possessed by these cells produces NO continuously at a constant level.

Although meant to be protective, reactive nitrogen intermediates can actually suppress host defenses during some infections, such as listeriosis and brucellosis, and thus play a pathogenic role in some infectious diseases. The NO pathway also may contribute to the destructive aspects of an immune response, particularly in chronic inflammation, by the nonspecific destruction of cellular metabolic machinery within a circumscribed area of NO release. Such nonspecific destruction, if excessive, can lead to any one of a number of inflammatory diseases or syndromes, including autoimmune diseases, such as rheumatoid arthritis.

Interfering with the production of NO provides a means of modulating inflammatory reactions and of inhibiting the destructive sequelae of a chronic inflammatory immune response. However, given that NO is highly reactive by nature, inhibitors which inhibit the NO radical directly would not be expected to be as effective as an inhibitor which blocks the synthesis of the NO radical.

It is an object of the present invention to provide a method for the treatment of chronic and acute inflammatory conditions, including autoimmune diseases. More specifically, it is an object of the present invention to provide a method for the treatment of such conditions wherein an agent that decreases the amount of nitric oxide present is administered. These and other objects and advantages of the present invention, as well as additional inventive features, will be apparent from the description of the invention provided herein.

SUMMARY OF THE INVENTION

The present invention provides a method for treating a mammal, preferably a human, having an inflammatory condition, especially chronic, wherein an effective amount of an agent, which is capable of decreasing the amount of nitric oxide present, is administered. Preferably, the agent is an inhibitor of nitric oxide synthase (NOS), a nitric oxide scavenger, or an inhibitor of tetrahydrobiopterin synthesis. More preferably, the NOS inhibitor is a L-arginine analog, such as $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, or aminoguanidine, or a cytokine, such as MDF, TGF-$\beta$1, TGF-$\beta$2, TGF-$\beta$3, IL-4, or IL-10. Even more preferably, the NOS inhibitor is N-iminoethyl-L-ornithine, citrulline, canaline, homocitrulline, aminoguanidine, MDF, or IL-10. The NO scavenger is preferably hemoglobin or ferrous diethyldithiocarbamate (DETC). The inhibitor of tetrahydrobiopterin synthesis is preferably 2,4-diamino-6-hydroxy-pyrimidine.

The inflammatory condition to be treated may be any one of a number of inflammatory conditions, such as rheumatoid arthritis, osteoarthritis, systemic lupus erythematosus, psoriasis, discoid lupus, collagen vascular disease, diabetes mellitus, myositis, polyarteritis, scleroderma, sarcoidosis, granulomatous lesions such as hepatic granulomas, inflammatory bowel disease, thyroiditis, multiple sclerosis, graft versus host disease, organ transplant rejection, sepsis, acute respiratory distress syndrome, cirrhosis, periodontitis, gingivitis, AIDS dementia, primary biliary cirrhosis, granulomatous hepatitis, Wegener's granulomatosis, chronic granulomatous disease, allergic granulomatosis, granulomatous arteritis-Polymyalgia rheumatica, and inflammation of the central nervous system.

DETAILED DESCRIPTION OF THE PREFERRED EMBODIMENTS

Figure 1:
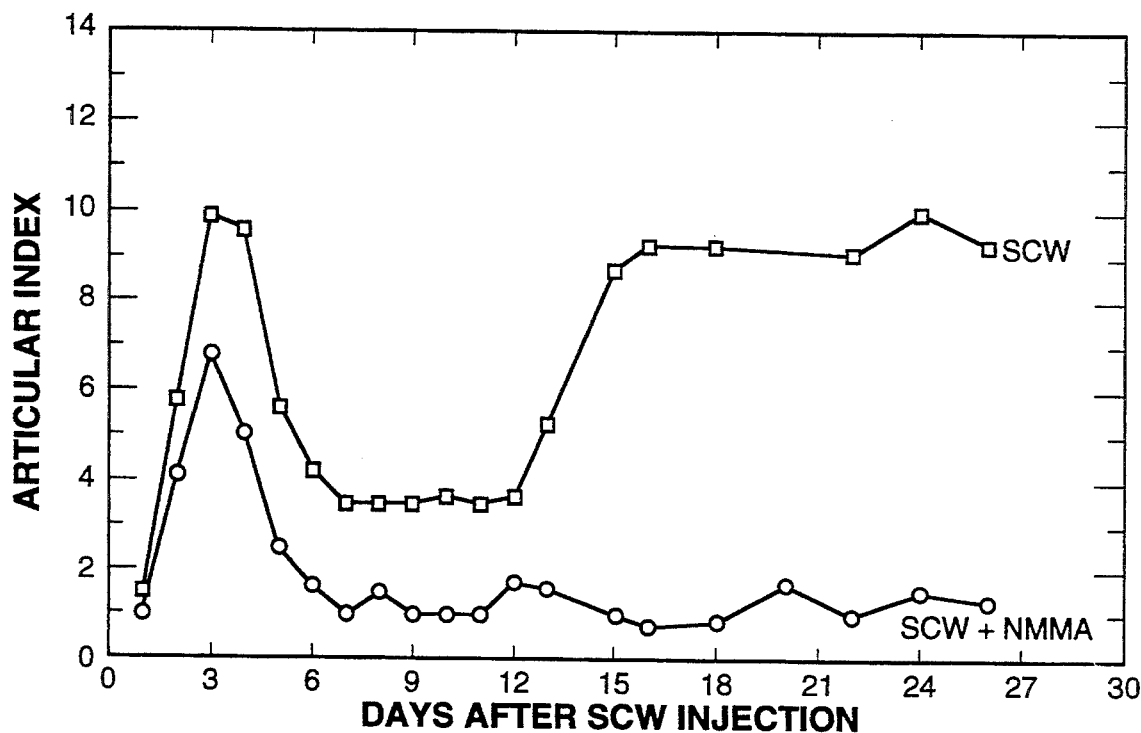
FIG. 1 is a graph of articular index versus days after injection with either SCW alone (SCW) or SCW in combination with NMMA (SCW+NMMA).

The present invention provides a method for treating a mammal having an inflammatory condition, whether acute or chronic but especially chronic, wherein the inflammatory condition involves the activation of leukocytes, which leads to an impairment of normal physiological function. The present inventive method comprises the administration of an effective amount of a compound such as a compound that inhibits NOS, a nitric oxide scavenger, or an agent that blocks the synthesis of tetrahydrobiopterin. Preferably, the NOS inhibitor is an L-arginine analog, such as $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, or aminoguanidine, or a cytokine, such as MDF, TGF-B1, TGF-β2, TGF-β3, IL-4, or IL-10. Even more preferably, the NOS inhibitor is N-iminoethyl-L-ornithine, citrulline, canaline, homocitrulline, aminoguanidine, MDF, or IL-10. The NO scavenger is preferably hemoglobin or ferrous diethyldithiocarbamate (DETC). The inhibitor of tetrahydrobiopterin synthesis is preferably 2,4-diamino-6-hydroxy-pyrimidine.

The method may be used to treat any one of a number of inflammatory conditions, including inflammatory conditions associated with autoimmune diseases, whether systemic or organ specific, immune disorders, and inflammatory conditions associated with hepatic granulomas. Specific examples of inflammatory conditions, which may be treated in accordance with the present inventive method include, but are not limited to, rheumatoid arthritis, osteoarthritis, systemic lupus erythematosus, psoriasis, discoid lupus, collagen vascular disease, diabetes mellitus, myositis, polyarteritis, scleroderma, sarcoidosis, granulomatous lesions such as hepatic granulomas, inflammatory bowel disease, thyroiditis, multiple sclerosis, graft versus host disease, organ transplant rejection, sepsis, acute respiratory distress syndrome, cirrhosis, periodontitis, gingivitis, AIDS dementia, and inflammation of the central nervous system. Diseases associated with hepatic granulomas include hepatobiliary disorders, such as primary biliary cirrhosis and granulomatous hepatitis, in which cases the hepatic granulomas arise secondary to inflammation or immune system dysfunction. Other diseases associated with hepatic granulomas include those diseases which originate as inflammatory or autoimmune disorders, such as Wegener's granulomatosis, allergic granulomatosis, and granulomatous arteritis-Folymyalgia rheumatica, in addition to sarcoidosis, inflammatory bowel disease, and chronic granulomatous disease as mentioned above.

The dose administered to an animal, particularly a human, in the context of the present invention should be sufficient to effect a prophylactic or therapeutic response in the animal over a reasonable time frame. One skilled in the art will recognize that the preferred dosage will depend upon a variety of factors including the strength of the particular compound employed, the condition of the animal, the body weight of the animal, as well as the severity of the inflammation. The size of the dose will also be determined by the existence, nature, and extent of any adverse side-effects that might accompany the administration of a particular compound. The dose should be sufficient to alleviate inflammation and tissue damage of the patient. When $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, or aminoguanidine is administered to treat the inflammatory condition, the effective amount is typically from about 1 to about 100 mg/kg/day. When hemoglobin or DETC is administered to treat the inflammatory condition, the effective amount is typically from about 1 to about 25 grams per dose. An effective amount of 2,4-diamino-6-hydroxy-pyrimidine is typically from about 0.1 to about 1000 μg/kg/day. Typically, an effective amount from about 0.1 to about 100 μg/kg/day of MDF, TGF-β1, TGF-β2, TGF-β3, IL-4, or IL-10 can be administered to treat the inflammatory condition.

While the present inventive method may be practiced on any mammal using any suitable means of administration, the present invention is particularly applicable to humans using a parenteral route of administration. Even more preferably, the administration is intravenous.

L-arginine analogs, which inhibit NOS, are listed in Table 1. These compounds inhibit NO synthesis by effectively blocking inducible nitric oxide synthesis and release at the site of inflammation (see Example 2), thereby reducing the destructive pathology of chronic inflammation. For example, the administration of a methyl derivative of arginine, such as $N^G$-monomethylarginine (NMMA), to mammals with erosive polyarthritis suppresses joint disease, inflammation, tissue swelling, and bone and cartilage degradation as shown in Example 3. NMMA also suppresses liver granulomas and fibrosis as shown in Example 4. This immunosuppressive activity of NMMA in inflammation is consistent with its ability to block leukocyte secretion of NO in vitro as shown in Example 5. Moreover, no apparent side effects were observed during therapy with the inhibitor NMMA.

TABLE 1

L-arginine Analogs Which Inhibit NO Synthesis

L-NMMA: $N^G$-monomethyl-L-arginine
L-NAME: $N^G$-nitro-L-arginine methyl ester
L-NA (L-NNA): $N^G$-nitro-L-arginine
L-NIO: N-iminoethyl-L-ornithine
L-NAA: $N^G$-amino-L-arginine
L-canavanine (specific for phagocytic cells)
Citrulline: 2-amino-5-ureidovaleric acid
Canaline: α-amino-γ[amino-oxy]-n-butyric acid (an ornithine derivative)
Homocitrulline (a citrulline analog having an additional $CH_2^-$ group)
Aminoguanidine L-NMMA is commercially available from Calbiochem. L-NAME, L-NA, L-canavanine, citrulline, canaline, and aminoguanidine are all commercially available from Sigma. Homocitrulline is available from United States Biochemical Corporation. L-NIO is not commercially available; however, it may be synthesized following the methods recited in Acta Biochem. Biophys. Acad. Sci. Hung., 12, 191–196 (1977), or isolated from fermentation broth following the procedures recited in J. Antiobiot., 25, 179–184 (1972). L-NAA also is not commercially available; however, it may be synthesized by following the methods described in Biochem. Biophys. Res. Com., 170, 96 (1990), or Biochem. Biophys. Res. Com., 168, 458 (1990).

Cytokines, which inhibit NOS, are listed in Table 2. Preliminary evidence suggests that cytokines suppress NOS at the level of gene expression. The absence of NOS gene expression also results in suppression of inflammation.

TABLE 2

Cytokines: Interfere With Induction of NOS

Macrophage deactivation factor (MDF)
Transforming growth factors (TGF-β1, 2, 3)
Interleukin 4 (IL-4)
Interleukin 10 (IL-10)

MDF is not commercially available; however, J. Exp. Med., 171, 1347 (1990), describes a purification method for MDF. TGF β1, 2, and 3 are available from R&D Systems and Celtfix. IL-4 and IL-10 are available from Schering-Plough.

Compounds, such as hemoglobin (available from Biopure Corp./Upjohn or Somatogen) and ferrous DETC (Sigma), are NO scavengers. NO scavengers interfere with the aggregate activity or effects of NO by reducing the amount of NO available to the tissues. Such compounds are set forth in Table 3.

TABLE 3

NO Scavengers

Hemoglobin
Ferrous diethyldithiocarbamate (DETC)

Agents that inhibit tetrahydrobiopterin synthesis include, for example, 2,4-diamino-6-hydroxypyrimidine (Sigma). 2,4-diamino-6-hydroxypyrimidine inhibits GTP cyclohydrolase I, an enzyme that is involved in the transformation of GTP to tetrahydrobiopterin. Tetrahydrobiopterin is an essential cofactor for NOS. Accordingly, by inhibiting the synthesis of an essential cofactor of NOS, the activity of NOS is impaired, and NO is not synthesized.

All of the above compounds are effective in reducing nitrite levels and, therefore, can be used to modulate an inflammatory response and to inhibit the destructive sequelae of a chronic inflammatory immune response. It is expected, however, that inhibitors of NO synthesis are more effective than inhibitors of NO, itself, given the highly reactive nature of the NO radical. Accordingly, the preferred target is NOS, the enzyme responsible for NO production. A constitutive form of this enzyme is present in neurons and endothelial cells, whereas an inducible form of this enzyme is present in macrophages, which accounts for the ability of macrophages to produce large quantities of NO upon stimulation.

Treatment of a patient with the method of the present invention involves administering a therapeutic or effective amount of one or more of the above NO inhibitors. The present inventive method enables the alleviation, slowing of the progression, prophylaxis, attenuation, or cure of the existing disease. Subjective improvement, such as decreased pain or improved vigor, is indicative of effective treatment. Objective improvement, such as decreased joint or soft tissue swelling or improvement in laboratory parameters or radiographic studies, is also indicative of effective treatment.

It will be appreciated by one who is skilled in the art that the above compounds can be administered alone or in combination with one or more of the other above compounds. It will also be appreciated by one of skill in the art that the above compounds can be administered with other known compounds, which are useful in the treatment of inflammation, such as, for example, pain killers.

The compounds of the present inventive method may be formulated with conventional pharmaceutically acceptable parenteral vehicles for administration by injection. These vehicles comprise substances, which are essentially nontoxic and nontherapeutic, such as water, saline, Ringer's solution, dextrose solution, Hank's solution, and the like. Formulations may also include small amounts of adjuvants, such as buffers and preservatives, to maintain isotonicity and physiological and pH stability.

The compounds of the present inventive method also may be delivered or administered topically, by transdermal patches, intravenously, intraperitoneally, locally, intra-articularly, in aerosol form, orally, or in drops, among other methods. Intravenous administration is preferred. When the agent is administered intravenously, it can be delivered as a bolus, a short term infusion or as a continuous infusion. Some examples of local administration include injection into a muscle, tendon, or cyst. Intraarticular injection or injection into a joint or joint space may be preferred in certain cases of arthritis.

The following examples further illustrate the present invention and, of course, should not be construed as in any way limiting its scope.

EXAMPLE 1

This example describes the induction of erosive polyarthritis in female Lewis rats, which serves as a valid preclinical model for an inflammatory condition, such as rheumatoid arthritis.

Group A streptococci from the American Type Culture Collection (SCW; ATCC 10389) were grown in Todd Hewitt Broth (Difco, Detroit, Mich.), harvested in log phase, washed with phosphate-buffered saline (PBS), incubated twice at 50° C. with 4% sodium dodecyl sulfate (SDS), washed extensively to remove the SDS, and incubated sequentially with DNase, RNase, and trypsin (4 hours at 37° C. each; reagents available from Sigma). The washed cell walls were sonicated for 70 minutes, and the cell wall fragments (SCW) remaining in the supernatant after half an hour of centrifugation at 10,000 gravity (g) were utilized for injection. The total amount of rhamnose in the cell wall contained in the supernatant was determined by the Dische-Shettles method (J. Biol. Chem., 175, 595-603 (1948)).

Female Lewis rats were obtained from Harlan Sprague Dawley, Indianapolis, Ind. On day 0, each rat was injected intraperitoneally (i.p.) with an aqueous suspension of SCW (J. Clin. Invest., 76, 1042–1056 (1985); J. Exp. Med., 168, 1403–1417 (1988)). The injected arthropathic dose, i.e., injected dose capable of inducing arthritis, was equivalent to 30 μg of cell wall rhamnose per gram of body weight. Rhamnose is 6-deoxy-L-mannose, $C_6H_{12}O_5$. Control animals received an equal volume of PBS.

Systemic administration of an aqueous suspension of SCW, or peptidoglycan-polysaccharide fragments, induced a bimodal pattern of arthritis in susceptible rats coincident with the deposition and persistence of SCW antigens in the synovium. The acute reaction occurred within 24 hours, reached maximum severity within 3–5 days, and then subsided (see SCW line in FIG. 1). Histologically, the acute phase was characterized by extensive fibrin deposition, edema, and neutrophil infiltration.

Within the next two weeks, an exacerbation of the arthritis occurred. This chronic, T cell-dependent phase persisted and was characterized by intense infiltration of inflammatory mononuclear cells, extensive hyperplasia of the synovial lining cells, and erosive destruction of subchondral and periarticular bone and cartilage. The distribution and pathologic and radiologic profiles of this experimental arthritis model exhibited many similarities to rheumatoid arthritis, and it is considered to be a valid preclinical model.

EXAMPLE 2

This example demonstrates that nitrites are generated locally in the inflammatory lesions, which result from an inflammatory condition.

Female Lewis rats were rendered arthritic as described in Example 1. Synovial tissue was then removed and grown in tissue culture. Synovial tissue was also removed from nonarthritic rats for use as control tissue.

Figure 2:
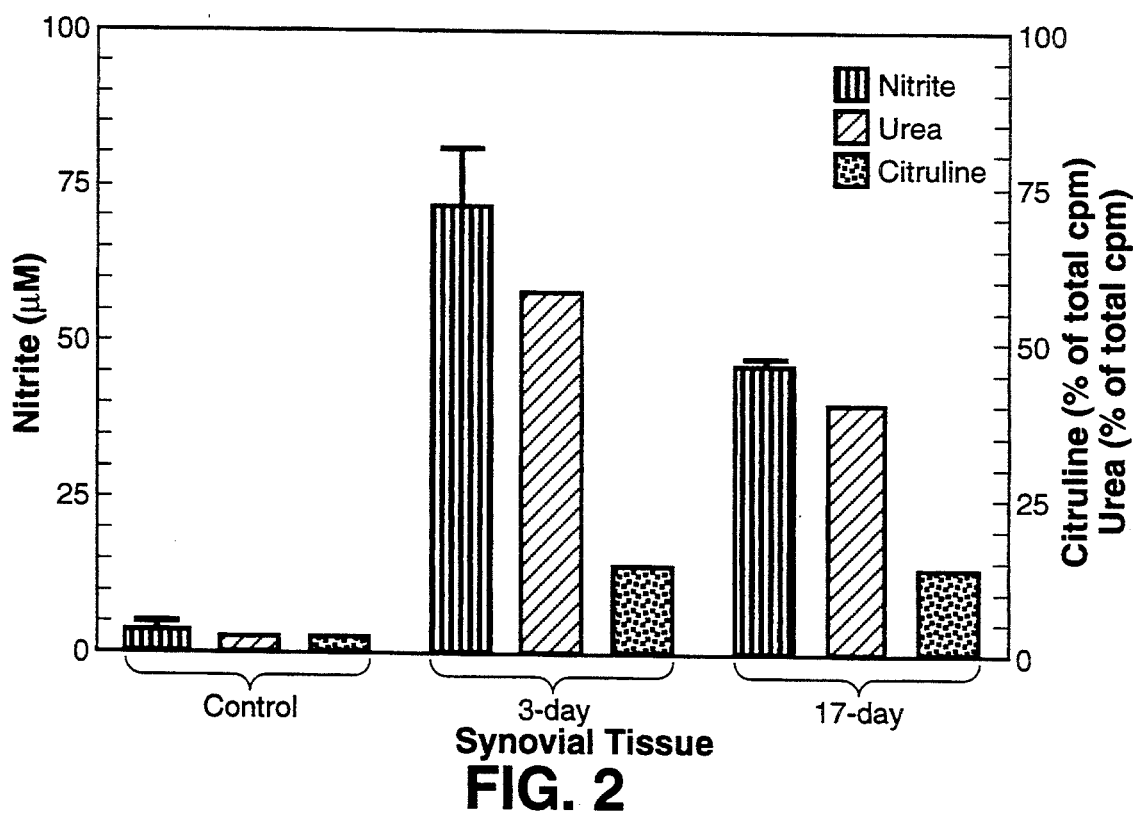
FIG. 2 is a bar graph of nitrite concentration ($\mu$M), citrulline (% of total cpm), and urea (% of total cpm), versus synovial tissue 3 days and 17 days post-injection and a control sample.

Given that nitric oxide has a very brief half-life and is, therefore, extremely difficult to measure, citrulline, a byproduct of the NO pathway, and nitrite, a breakdown product of NO, were used as an indication of NO production. [Guanido-$^{14}$C]-L-arginine (50 nCi/well, DuPont) was added to the tissue cultures to determine the metabolism of L-arginine during culture. The presence of $^{14}$C-citrulline indicates that the NO was produced by the metabolism of arginine by way of the NOS pathway, whereas the presence of $^{14}$C-urea indicates the metabolism of arginine by the arginase pathway. Nitrite concentrations in culture supernatants were measured with Griess reagent and interpreted as a reflection of the flux of L-arginine through the NOS pathway. Labelled urea and citrulline in the culture supernatants were separated by HPLC using an automated amino acid analyzer and measured as the fraction (percentages) of total counts per minute (cpm) found in these compounds at the end of culture (J. Surgical Research, 50, 403–409 (1991); see FIG. 2).

Acutely inflamed tissue, such as that three days post-injection, included mainly a neutrophilic infiltration. Chronically inflamed tissue, such as that 17 days post-injection, included mainly T-cell and monocyte or macrophage infiltration. The data in FIG. 2 indicate that the NOS pathway is operative in both acutely and chronically inflamed tissues and, therefore, nitrites are generated locally in the inflammatory lesions.

EXAMPLE 3

This example demonstrates that NOS inhibitors, such as $N^G$-monomethyl-L-arginine (NMMA) and aminoguanidine, reduce inflammation in vivo.

Six female Lewis rats received a single dose of SCW at day 0 as described in Example 1, and were treated daily with intravenous injections of 30 mg/kg NMMA beginning on day 0 (see FIG. 1, SCW+NMMA). Six other female Lewis rats received only SCW (see FIG. 1, SCW).

The severity of the arthritis manifested by each animal was determined using a "joint count" (Articular Index, AI). This score is derived by the summation of a score of 0 (normal) to 4 (maximum) for each extremity based on the degree of swelling, erythema, and degree of distortion (maximum total score of 16). The animals were checked daily during the acute response and every other day thereafter. All animals were examined by routine histologic techniques. Joints were either fixed in 10% formalin, decalcinated, sectioned, and stained with hematoxylin and eosin or quick-frozen in O.C.T. compound (Miles Scientific, Naperville, Ill.) by immersion in a mixture of dry ice and acetone for additional staining.

Daily intravenous injections of NMMA from the onset of arthritis resulted in a marked suppression of the articular index. The AI of the NMMA-treated animals (SCW+NMMA) was reduced 80–90% as compared to the untreated arthritic animals (SCW, FIG. 1).

While acute inflammation was suppressed, the NMMA had a greater effect on the chronic phase of the disease. This has important therapeutic implications, since the chronic destructive arthritis is clinically more relevant and is mediated by T-lymphocytes and macrophages, which are the major source of inducible NO synthase activity. The data implicate macrophage-derived NO as a central mediator of synovial pathology.

Figure 3:
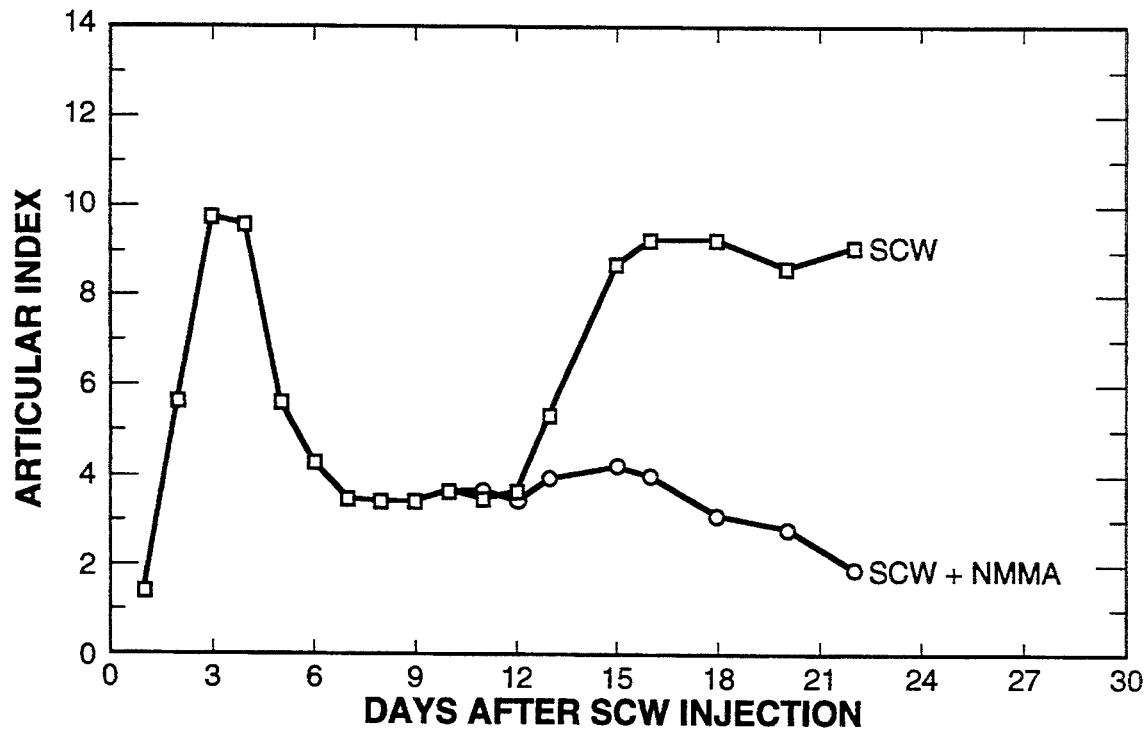
FIG. 3 is a graph of articular index versus days after injection with SCW. The SCW line follows the articular index over 22 days after injection with SCW, whereas the SCW+NMMA line follows the articular index over 12 days after injection with SCW, at which point the animals were injected with NMMA, and then over the 10 days following injection with NMMA.

If NMMA were not administered until arthritis had already proceeded past the acute phase, the NO synthase inhibitor could still effectively reverse the course of the arthritis (see FIG. 3, SCW+NMMA). Animals were injected with an arthropathic dose of SCW on day 0. Twelve days later (FIG. 3 arrow), treatment with NMMA was initiated. AI were determined for treated and untreated animals and represent the means for 6 animals.

Synovial tissue from both groups of animals (FIGS. 1 and 3) was examined histologically. The synovia from the NMMA-treated, SCW-injected animals exhibited less inflammatory cell infiltrate, less synovial hyperplasia, and less evidence of erosions than the untreated arthritic animals.

Figure 4:
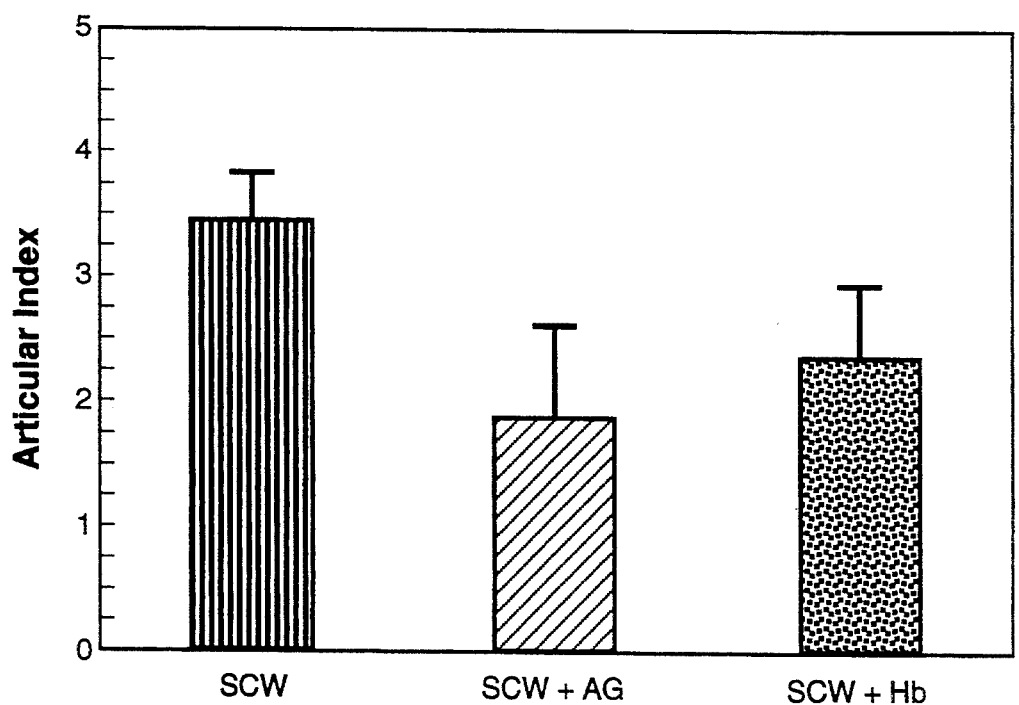
FIG. 4 is a bar graph of articular index versus treatment with SCW alone (SCW), SCW and aminoguanidine (SCW+AG), and SCW and hemoglobin (SCW+Hb).

Injection of arthritic animals with 5 mg aminoguanidine (SCW+AG) also resulted in the reduction of AI as compared to untreated arthritic animals (SCW, FIG. 4).

cl EXAMPLE 4

This example demonstrates that NOS inhibitors, such as NMMA, suppress formation of liver granulomas and hepatic fibrosis in vivo.

Figure 5:
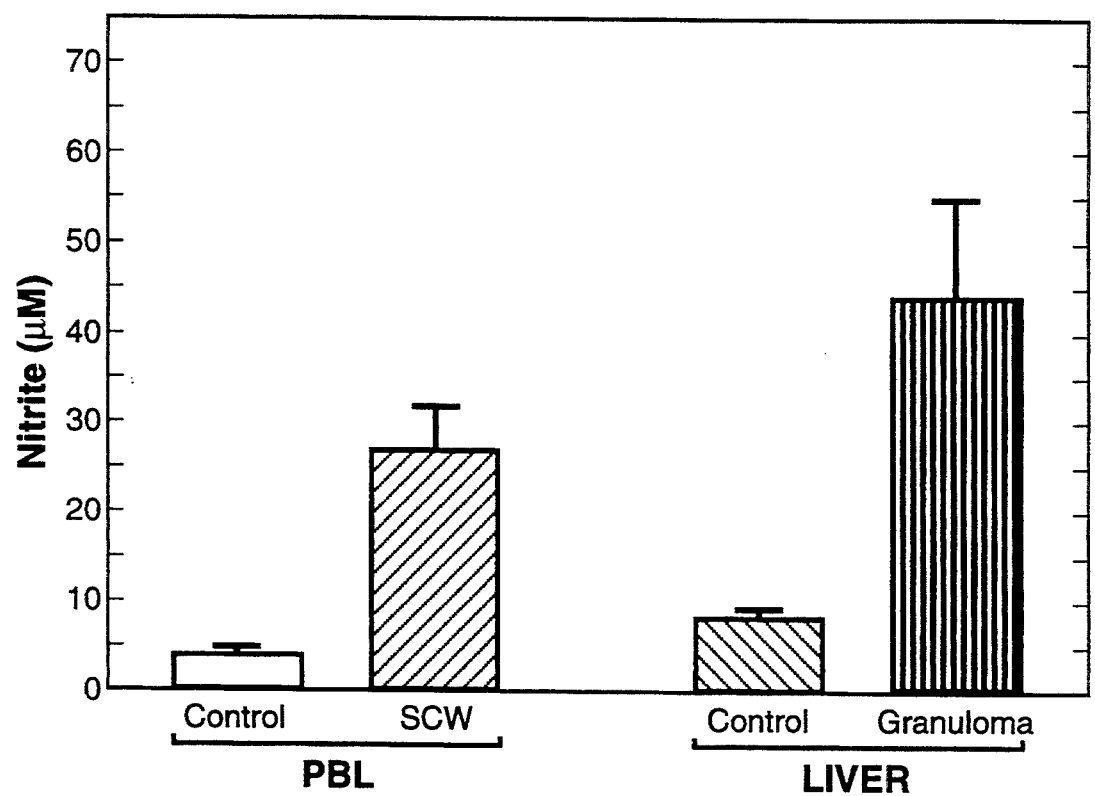
FIG. 5 is a bar graph of nitrite concentration ($\mu$M) versus untreated (PBL, control) and SCW-treated (PBL, SCW) peripheral blood leukocytes and untreated (LIVER, control) and granulomatous (LIVER, granuloma) liver.

Female Lewis rats were rendered arthritic as described in Example 1. A separate group of female Lewis rats, which served as a control group, was injected with PBS. Peripheral blood and liver tissue were isolated from the arthritic animals and the untreated control animals. Peripheral blood leukocytes (PBL) and liver tissue from arthritic (SCW, GRANULOMA) and control (CONTROL) animals were cultured in DMEM without SCW. The liver tissue from arthritic animals constitutively expressed NOS pathway products and showed granuloma formation and subsequent hepatic fibrosis (see FIG. 5).

Female Lewis rats received a single dose of SCW or PBS at day 0 and were treated with NMMA for either days 0 through 4, 12 through 26, or 0 through 26. A dose of 30 mg/kg body weight of NMMA was administered intravenously daily. After the treatment, the animals were sacrificed and their livers were evaluated for granuloma formation (see Table 5). Untreated control animals (Control) and animals treated only with NMMA (NMMA) showed no development of liver granulomas. Animals treated only with SCW (SCW) showed extensive development of liver granulomas. Animals treated with both SCW and NMMA (SCW+NMMA) showed minimal or no development of liver granulomas. Treatment with NMMA was effective both at the acute (0–4 days after injection with SCW) and chronic phases of inflammation. Thus, NMMA suppressed the formation of bacterial cell-wall induced liver granulomas and hepatic fibrosis.

TABLE 5

Suppression of Hepatic Granulomas
by $N^G$-monomethyl-arginine (NMMA)

| Treatment | Liver Granulomas |
| --- | --- |
| Control | 0 |
| NMMA | 0 |
| SCW | ++++ |
| SCW + NMMA (day 0–4) | ± |
| SCW + NMMA (day 12–26) | 0 |
| SCW + NMMA (day 0–26) | ± |

The animals were also evaluated for their percentage hematocrit and white blood cell (WBC) count (see Tables 6 and 7, respectively). The data show that SCW treatment (SCW) significantly depressed percent hematocrit and elevated the white blood cell count, thus producing both anemia and leukocytosis. Treatment with NMMA in conjunction with SCW (SCW+NMMA) inhibited the anemia and the leukocytosis as compared to the untreated SCW animals (SCW). This was true for both acutely and chronically inflamed tissues. However, leukocytosis was particularly inhibited in chronically inflamed tissues.

TABLE 6

$N^G$-monomethyl-arginine Inhibition
of SCW-Induced Anemia

| Treatment | Hematocrit % |
| --- | --- |
| PBS | 49.3 |
| NMMA | 47.3 |
| SCW | 33.2 |
| SCW + NMMA (day 0–4) | 41.3 |
| SCW + NMMA (day 0–26) | 40.8 |
| SCW + NMMA (day 12–26) | 44.5 |

TABLE 7

$N^G$-monomethyl-arginine Inhibition
of SCW-Induced Leukocytosis

| Treatment | WBC (cells × $10^6$/ml) |
| --- | --- |
| PBS | 12.8 |
| NMMA | 8.3 |
| SCW | 95.9 |
| SCW + NMMA (day 0–4) | 28.7 |
| SCW + NMMA (day 0–26) | 23.2 |
| SCW + NMMA (day 12–26) | 15.9 |

EXAMPLE 5

This example demonstrates that NOS inhibitors, such as NMMA, canaline, canavanine, aminoguanidine, and N-nitro-L-arginine methyl ester (NAME), reduce nitrite production by leukocytes in vitro.

Female Lewis rats were rendered arthritic as described in Example 1. A separate group of female Lewis rats, which served as a control group, was injected with PBS. Peripheral blood was isolated from the arthritic animals and the untreated control animals.

Mononuclear cells were isolated from heparinized peripheral blood by density gradient centrifugation through Ficoll (Sigma), a nonionic synthetic polymer of sucrose. The isolated cells were suspended in phenol red-free Dulbecco's modified Eagle's Medium (DMEM, available from Cellgro) containing 50 μg/ml gentamicin sulfate and 2 mM glutamine and supplemented with 100 μM L-arginine. Cells (1–3×$10^6$/ml) were plated in 24-well plates (Costar Corp., Cambridge, Mass.) and cultured for 24–48 hours in the presence of SCW (prepared as in Example 1) and 10, 100, or 500 μM NMMA.

Peripheral blood leukocytes were also isolated from untreated female Lewis rats and cultured in DMEM. Some of these cultured cells were then treated with 0.1–1.0 μg/ml SCW to serve as an experimental cell population. The remaining cultured cells were left untreated for use as a control cell population. The SCW-treated cells were further treated with either 500 μM canaline, canavanine, NAME, or aminoguanidine (all L-arginine analogs available from Sigma).

Adherent cells were fixed for 15 minutes with 4% paraformaldehyde in PBS for subsequent staining for NADPH diaphorase activity and in situ hybridization. Culture supernatants were collected for quantitation of nitrite production by the Griess reaction, a colorimetric microtiter plate method (Rockett et al., Infection and Immunity, 59, 3280 (1991)).

Nitrite production was quantitated by incubating equal volumes (50 μl ) of supernatant fluid and Griess reagent (1% sulfanilamide/0.1% naphthylene diamine dihydrochloride/2.5% $H_3PO_4$) for 10 minutes at room temperature. Absorbance was read on a microplate reader (Dynatech) with a test wavelength of 540 nanometers (nm) and a reference wavelength of 610 nm. The concentration of nitrite was determined from a standard curve using dilutions of a stock sodium nitrite solution (200 μM). Samples were tested in triplicate and reported as the mean concentration ±SEM.

Figure 6A:
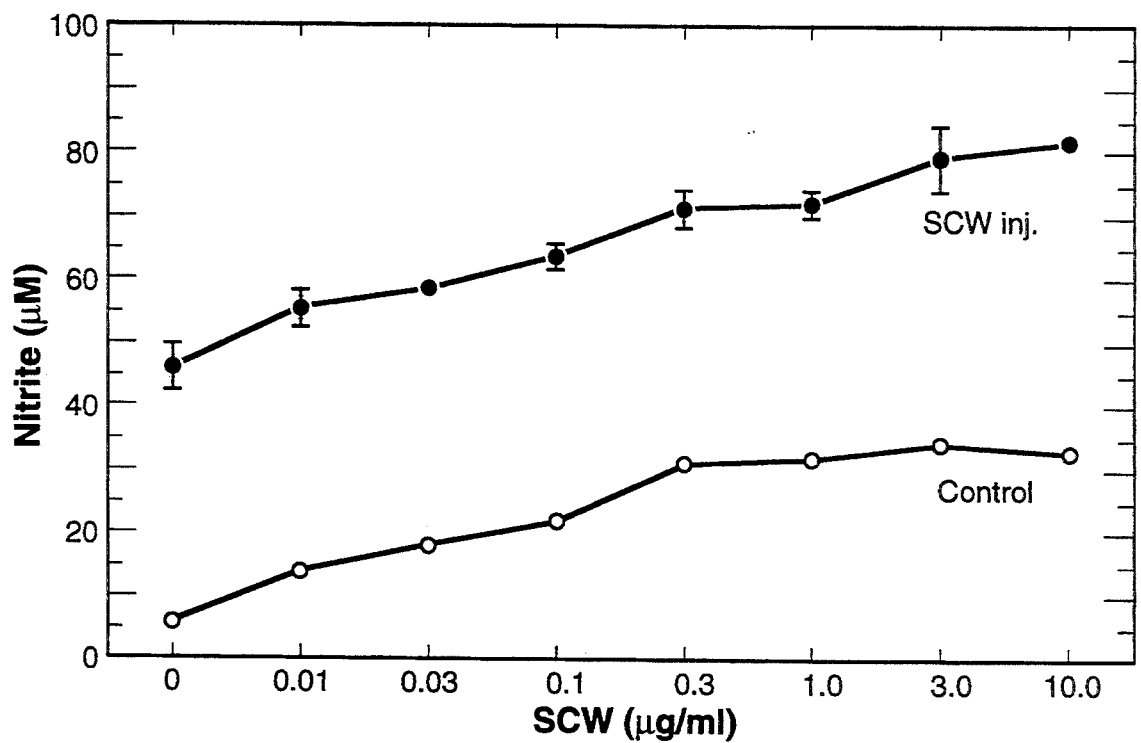
FIG. 6A is a graph of nitrite concentration (μM) versus SCW concentration (μg/ml) for control (Control) and SCW-treated animals (SCW Inj.).
Figure 6B:
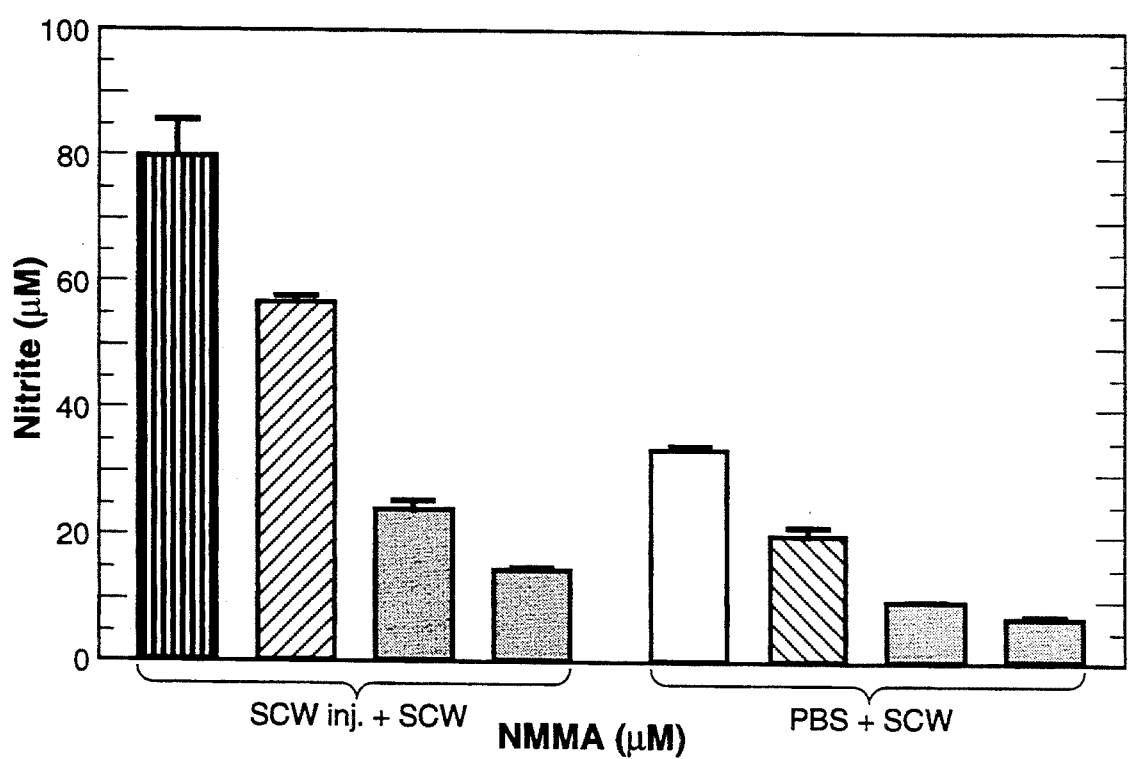
FIG. 6B is a bar graph of nitrite concentration (μM) versus NMMA concentration (μM) for arthritic animals (SCW inj.+SCW) and control animals (PBS+SCW).

The cells from the arthritic animals (SCW Inj., FIG. 6A) produced a significantly greater amount of nitrite in comparison to cells from the control animals. Both experimental and control cell populations showed an increase in nitrite production as the concentration of SCW was increased in the culture medium. The cells obtained from untreated animals and treated with SCW (SCW) in culture also produced significantly greater amounts of nitrite as compared to cells obtained from untreated animals and not treated with SCW (Control, FIG. 7A). The cells from the arthritic animals and the cells from the control animals also demonstrated a significant reduction in nitrite production upon NMMA addition.

Figure 7A:
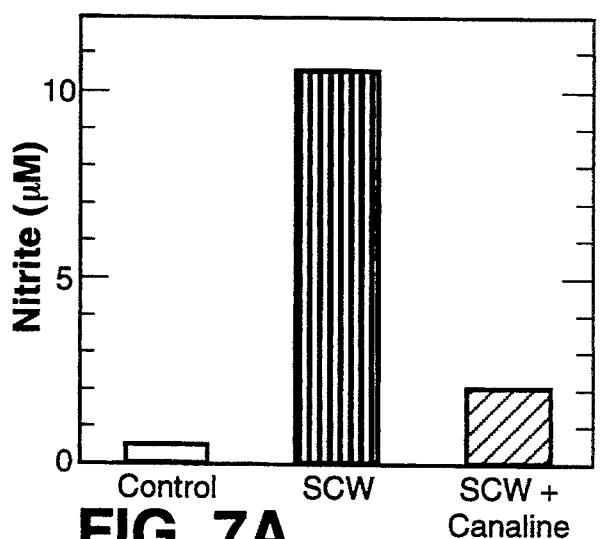
FIGS. 7A, B, and C are bar graphs of nitrite concentration (μM) versus cells obtained from untreated animals and animals treated with SCW and either canaline (SCW+Canaline, FIG. 7A), canavanine (SCW+Canavanine, FIG. 7B), NAME (SCW+NAME, FIG. 7B), or aminoguanidine (500 or 100 μM Aminoguanidine+SCW, FIG. 7C) in culture.
Figure 7B:
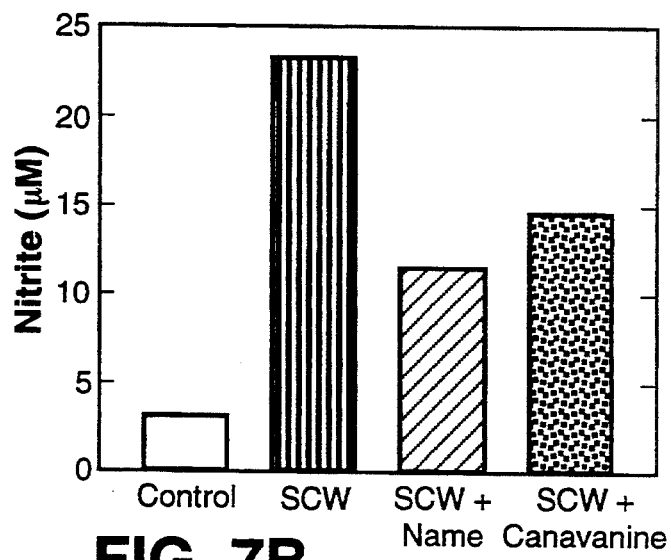
Figure 7C:
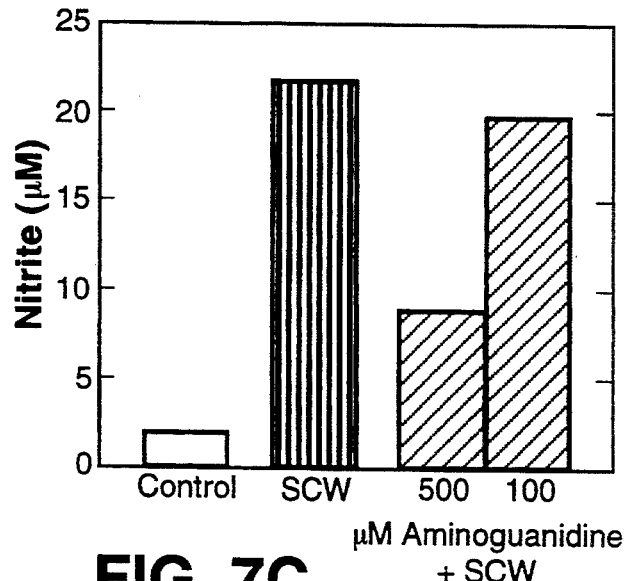

The cells obtained from untreated animals and treated with SCW and either canaline (SCW+Canaline, FIG. 7A), canavanine (SCW+Canavanine, FIG. 7B), NAME (SCW+NAME, FIG. 7B), or aminoguanidine (500 or 100 μM Aminoguanidine SCW, FIG. 7C) in culture produced substantially reduced levels of nitrites compared to cells obtained from untreated animals and treated with SCW alone (SCW, FIGS. 7A-C).

EXAMPLE 6

This example demonstrates that cytokines, such as the transforming growth factor-β (TGF-β) and IL-4, reduce inflammation in vivo.

Figure 8:
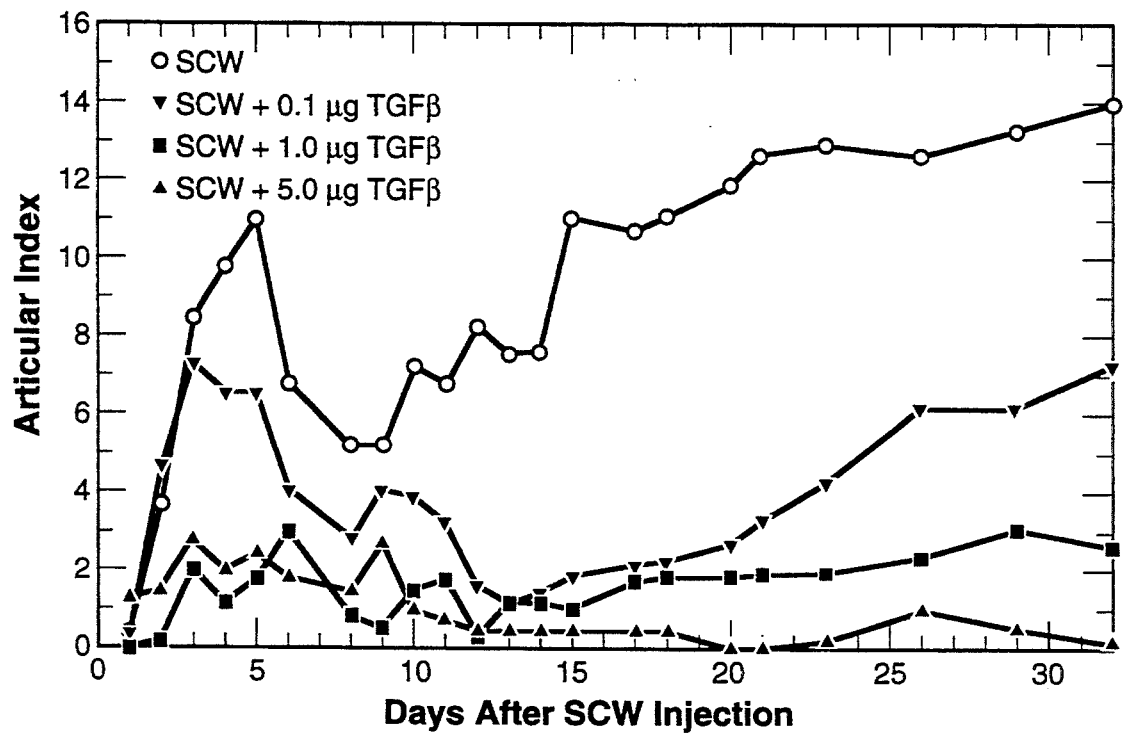
FIG. 8 is a graph of articular index versus days after SCW injection for SCW alone and in combination with different concentrations of TGF-β.

Female Lewis rats received a single dose of SCW on day 0 as described in Example 1. Groups of these animals were given intraperitoneal injections of either 0.1 μg (▼, FIG. 8), 1.0 μg (■, FIG. 8), or 5.0 μg (▲, FIG. 8) of TGF-β (Celtrix) daily beginning on day 0 or no TGF-β (o, FIG. 8). All of the TGF-β-treated arthritic animals showed significantly lower articular indices than untreated arthritic animals.

Figure 9:
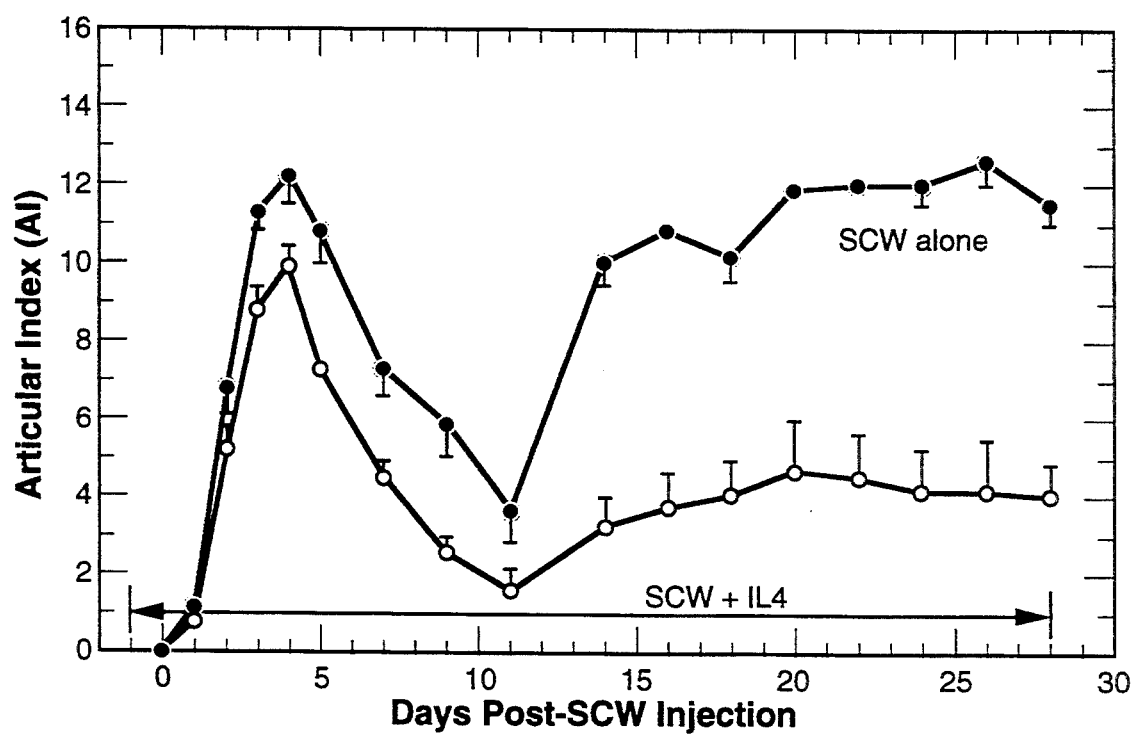
FIG. 9 is a graph of articular index versus days after SCW injection for SCW alone and with IL-4.

Some groups of arthritic rats were treated twice a day with 100 ng injections of IL-4 (Schering-Plough, SCW+IL-4, o, FIG. 9). Animals that were treated with SCW and IL-4 showed significant reduction in their articular indices, particularly in chronic inflammation, as compared to animals that were not treated with IL-4 (SCW alone, ●, FIG. 10).

Figure 10:
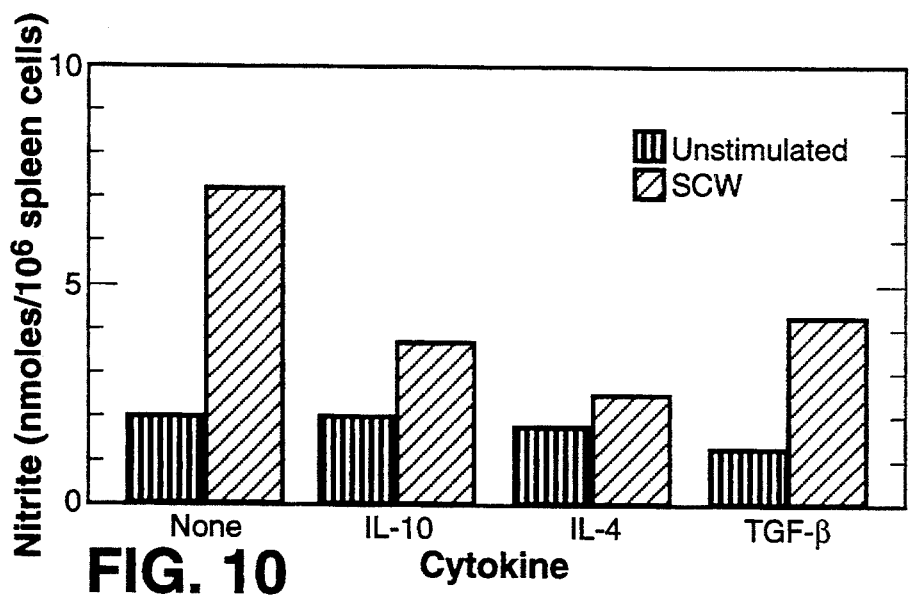
FIG. 10 is a bar graph of nitrite concentration (nmoles/$10^6$ spleen cells) versus untreated and SCW-treated cells, both of which were subsequently left untreated or treated with either IL-10, IL-4, or TGF-β.

The effectiveness of IL-10, IL-4, and TGF-β in reducing nitrite levels in comparison to control cells, both SCW-stimulated and unstimulated, is shown graphically in FIG. 10.

EXAMPLE 7

This example demonstrates that cytokines, such as the transforming growth factors β1, 2, and 3 (TGF-β1, 2, 3), inhibit the induction of NOS in vitro.

Figure 11:
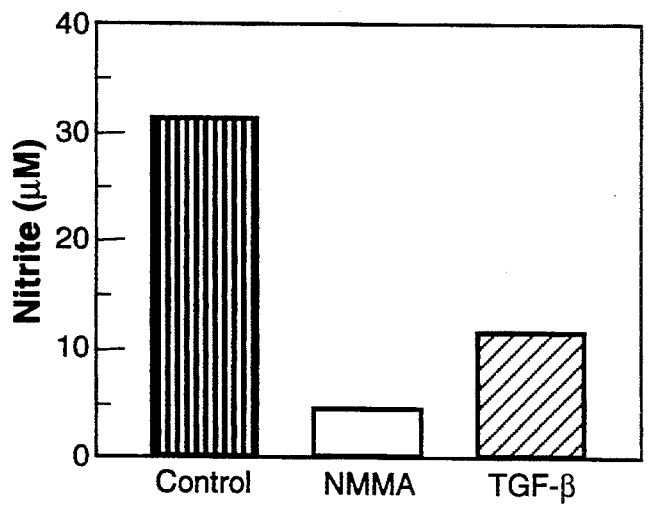
FIG. 11 is a bar graph of nitrite concentration (μM) versus untreated peripheral blood leukocytes (control), NMMA-treated leukocytes (NMMA), and TGF-β-treated leukocytes (TGF-β).

Peripheral blood leukocytes from arthritic female Lewis rats, which were obtained in accordance with Example 1, were grown in DMEM supplemented with SCW as described in Example 5. NMMA (500 μM, Calbiochem), TGF-β1 (10 ng/ml, FIG. 11, Cetrix Pharmaceuticals), or nothing (Control, FIG. 1) was added to each culture. After about 48 hours, aliquots of the culture supernatants were tested for nitrite levels by Griess reaction as described in Example 5. The cytokine TGF-β substantially reduced nitrite production by peripheral blood leukocytes in vitro.

EXAMPLE 8

This example demonstrates that cytokines, such as interleukin 10 (IL-10), reduce nitrite levels in vitro.

Figure 12:
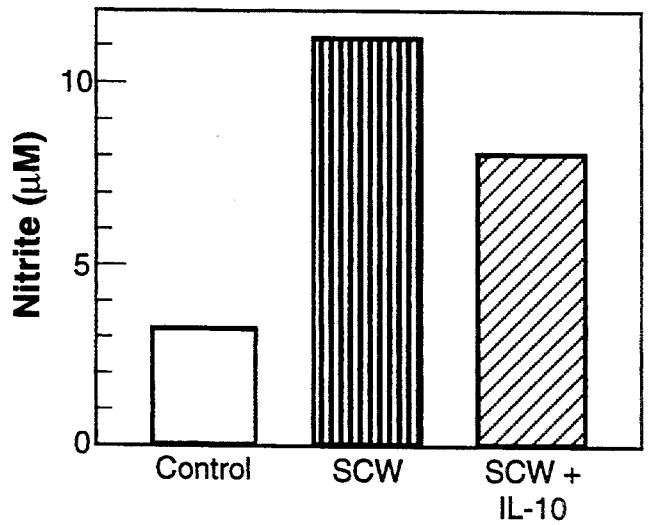
FIG. 12 is a bar graph of nitrite concentration (μM) versus untreated (control), SCW-treated (SCW), and SCW- and IL-10-treated (SCW+IL-10) peripheral blood leukocytes.

Peripheral blood leukocytes were grown in DMEM culture medium supplemented with SCW as described in Example 5. IL-10 (1,000 units, Genzyme) was added to some of the cultures. Treatment with IL-10 resulted in depletion of nitrites produced by the peripheral blood leukocytes (SCW+IL-10, FIG. 12) compared to SCW-treated peripheral blood leukocytes that were not treated with IL-10 (SCW, FIG. 12).

EXAMPLE 9

This example demonstrates that NO scavengers, such as hemoglobin, reduce inflammation in vivo.

Female Lewis rats received SCW on day 0 as described in Example 1. Some of these animals were also injected with 20 mg of hemoglobin (SCW+Hb). Other animals were left untreated (SCW). The articular indices of these animals were determined as described in Example 3. Hemoglobin reduced the articular index of arthritic animals.

EXAMPLE 10

This example demonstrates that NO scavengers, such as hemoglobin, reduce nitrite levels in vitro.

Figure 13:
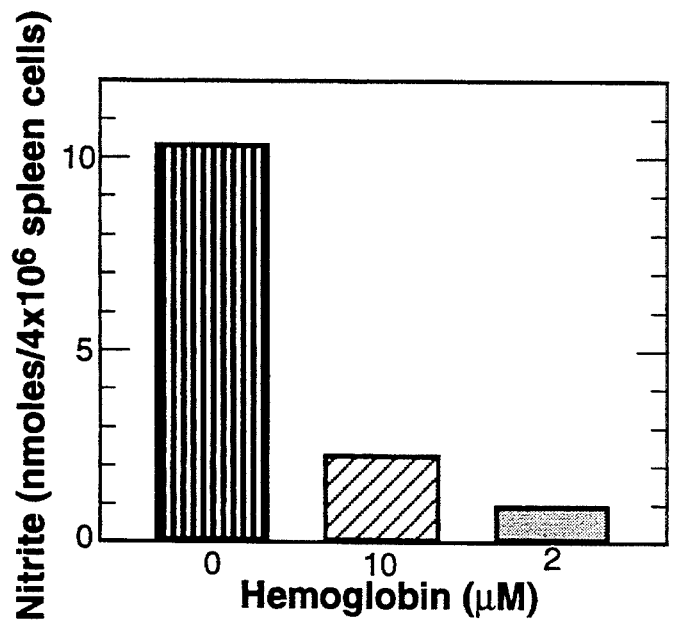
FIG. 13 is a bar graph of nitrite concentration (nmoles/$4 \times 10^6$ cells) versus hemoglobin concentration (0, 2, or 10 μM).

About $4 \times 10^6$ rat spleen cells were cultured in DMEM with 5 μg/ml SCW as described in Example 5. The spleen cells were cultured in the absence (0, FIG. 13) or presence of either 2 μM or 10 μM hemoglobin (2 or 10, FIG. 13, Sigma, Biopure, or Somatogen). After about 48 hours, aliquots of the culture supernatants were tested for nitrite levels by Griess reaction as described in Example 5. Cells treated with hemoglobin (2 or 10, FIG. 13) had reduced nitrite levels as compared to untreated control cells (0, FIG. 13).

EXAMPLE 11

This example demonstrates that inhibitors of tetrahydrobiopterin synthesis, such as 2,4-diamino-6-hydroxy-pyrimidine, reduce nitrite levels in vitro.

Figure 14:
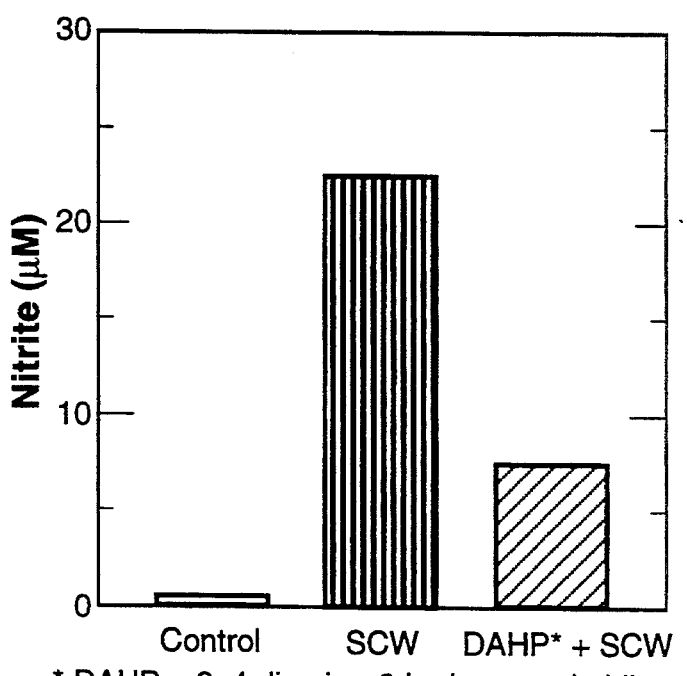
FIG. 14 is a bar graph of nitrite concentration (μM) versus 2,4-diamino-6-hydroxy-pyrimidine concentration (5 mM) and SCW concentration (2 μg/ml).

Peripheral blood leukocytes from control rats were grown in DMEM culture media in the absence (Control) or presence of 2 μg/ml SCW (SCW) and 5 mM 2,4-diamino-6-hydroxy-pyrimidine (DAHP+SCW, Sigma) (see FIG. 14). After 48 hours, aliquots of the culture supernatants were tested for nitrite levels by Griess reaction as described in Example 5. Cells treated with 2,4-diamino-6-hydroxy-pyrimidine had reduced nitrite levels as compared to untreated control cells.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method for treating a mammal having a chronic inflammatory condition comprising administering an effective amount of a compound selected from the group consisting of $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, and aminoguanidine wherein said condition is selected from the group consisting of arthritis, periodontitis, gingivitis, granulomas and fibrosis.

2. The method of claim 1, wherein said compound is selected from the group consisting of N-iminoethyl-L-ornithine, $N^G$-amino-L-arginine, citrulline, canaline, homocitrulline, and aminoguanidine.

3. The method of claim 2, wherein said effective amount is from about 1 to about 100 mg/kg/day.

4. The method of claim 2, wherein the administration is parenteral.

5. The method of claim 4, wherein the administration is intravenous.

6. A method for treating a mammal having rheumatoid arthritis comprising administering an effective amount of $N^G$-amino-L-arginine or aminoguanidine.

7. The method of claim 1, wherein said granulomas are granulomatous hepatitis, Wegener's granulomatosis, granulomatous disease, allergic granulomatosis, granulomatous arteritis-Folymyalgia rheumatica or hepatic granulomas.

8. The method of claim 7, wherein said hepatic granulomas are hepatobiliary disorders.

9. The method of claim 8, wherein said hepatobiliary disorders are primary biliary cirrhosis or granulomatous hepatitis.

10. A method for treating a mammal having chronic periodontitis and gingivitis comprising administering an effective amount of a compound selected from the group consisting of $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, and aminoguanidine.

11. A method for suppressing joint disease, inflammation, tissue swelling, and bone and cartilage degradation in a mammal having chronic arthritis comprising administering an effective amount of a compound selected from the group consisting of $N^G$-monomethyl-L-arginine, N-nitro-L-arginine methyl ester, $N^G$-nitro-L-arginine, N-iminoethyl-L-ornithine, $N^G$-amino-L-arginine, L-canavanine, citrulline, canaline, homocitrulline, and aminoguanidine.

* * * * *